(12) United States Patent
Cochran

(10) Patent No.: US 7,703,334 B2
(45) Date of Patent: Apr. 27, 2010

(54) BANDAGE TYPE SENSOR ARRANGEMENT AND CARRIER ASSEMBLY THEREFORE, AND METHOD OF MANUFACTURE

(75) Inventor: William T. Cochran, Clermont, FL (US)

(73) Assignee: Medility LLC, Clermont, FL (US)

( * ) Notice: Subject to any disclaimer, the term of this patent is extended or adjusted under 35 U.S.C. 154(b) by 27 days.

(21) Appl. No.: 11/906,851

(22) Filed: Oct. 4, 2007

(65) Prior Publication Data

US 2009/0090193 A1 Apr. 9, 2009

(51) Int. Cl.
*G01L 1/00* (2006.01)
(52) U.S. Cl. ..................................... 73/855
(58) Field of Classification Search ............ 73/855
See application file for complete search history.

(56) References Cited

U.S. PATENT DOCUMENTS

| | | | |
|---|---|---|---|
| 2,408,524 A | 10/1946 | Mestas | |
| 2,459,210 A | 1/1949 | Ashcroft | |
| 3,020,527 A | 2/1962 | MacLaren | |
| 3,268,845 A | 8/1966 | Whitmore | |
| 3,483,861 A | 12/1969 | Tiep | |
| 3,891,918 A | 6/1975 | Ellis | |
| 4,308,872 A | 1/1982 | Watson | |
| 4,373,534 A | 2/1983 | Watson | |
| 4,408,159 A | 10/1983 | Prox | |
| 4,777,962 A | 10/1988 | Watson | |
| 4,807,640 A | 2/1989 | Watson | |
| 4,813,435 A | 3/1989 | Arms | |
| 4,817,625 A | 4/1989 | Miles | |
| 4,838,868 A * | 6/1989 | Forgar et al. ............... 604/180 |
| 4,865,038 A | 9/1989 | Rich | |
| 5,036,275 A | 7/1991 | Muinch | |
| 5,069,221 A | 12/1991 | Smith | |
| 5,090,410 A | 2/1992 | Saper | |
| 5,159,935 A | 11/1992 | Sackner | |
| 5,170,786 A | 12/1992 | Thomas | |
| 5,209,230 A | 5/1993 | Swedlow | |
| 5,216,364 A | 6/1993 | Ko | |
| 5,217,012 A * | 6/1993 | Young et al. ............... 600/310 |
| 5,226,417 A | 7/1993 | Swedlow | |
| 5,329,932 A | 7/1994 | Yount | |
| 5,331,968 A | 7/1994 | Williams | |
| 5,497,147 A | 3/1996 | Arms | |
| 5,642,043 A | 6/1997 | Ko | |
| 5,760,577 A | 6/1998 | Shizuya | |

(Continued)

OTHER PUBLICATIONS

Micro-Epsilon, "Inductive Displacement Sensors and Gaging Sensors," Catalog of Micro-Epsilon, pp. 1-8.

(Continued)

*Primary Examiner*—Lisa M Caputo
*Assistant Examiner*—Octavia Davis
(74) *Attorney, Agent, or Firm*—Charles C. Krawczyk; Catherine A. Lewis

(57) ABSTRACT

A bandage type sensor arrangement wherein the sensor includes two parts movable with respect to each other, a carrier assembly is connected to the sensor parts for maintaining the sensor parts in place prior to use, and that is readily detachable for releasing the sensor parts while providing a connection of the sensor parts to a surface to be monitored. A cover is included as part of the carrier assembly to protect the operation of the sensor.

2 Claims, 10 Drawing Sheets

U.S. PATENT DOCUMENTS

| | | | |
|---|---|---|---|
| 5,777,467 A | 7/1998 | Arms | |
| 5,879,292 A | 3/1999 | Sternberg | |
| 5,902,250 A | 5/1999 | Verrier | |
| 5,914,593 A | 6/1999 | Arms | |
| 5,999,834 A * | 12/1999 | Wang et al. | 600/344 |
| 6,142,953 A | 11/2000 | Burton | |
| 6,179,159 B1 * | 1/2001 | Gurley | 221/26 |
| 6,340,884 B1 | 1/2002 | Wolf | |
| 6,356,075 B1 | 3/2002 | Shank | |
| 6,413,225 B1 | 7/2002 | Sackner | |
| 6,433,629 B2 | 8/2002 | Hamel | |
| 6,461,307 B1 | 10/2002 | Kristbjarnarson | |
| 6,479,986 B1 | 11/2002 | Steinich | |
| 6,529,127 B2 | 3/2003 | Townsend | |
| 6,551,252 B2 | 4/2003 | Sackner | |
| 6,622,567 B1 | 9/2003 | Hamel | |
| 6,678,543 B2 * | 1/2004 | Diab et al. | 600/323 |
| 6,694,160 B2 * | 2/2004 | Chin | 600/344 |
| 6,714,763 B2 | 3/2004 | Hamel | |
| 6,735,459 B2 * | 5/2004 | Parker | 600/344 |
| 6,781,366 B2 | 8/2004 | Hiramatsu | |
| 6,810,753 B2 | 11/2004 | Valdevit | |
| 6,810,754 B2 | 11/2004 | May | |
| 6,845,256 B2 | 1/2005 | Chin | |
| 6,926,679 B2 | 8/2005 | Friedrichs | |
| 6,941,162 B2 * | 9/2005 | Fudge et al. | 600/344 |
| 6,963,772 B2 | 11/2005 | Bloom | |
| 7,039,449 B2 | 5/2006 | Al-Ali | |
| 7,078,582 B2 | 7/2006 | Stebbings | |
| 7,225,007 B2 * | 5/2007 | Al-Ali et al. | 600/344 |
| 2005/0093537 A1 | 5/2005 | Townsend | |
| 2007/0142717 A1 * | 6/2007 | Lowery et al. | 600/323 |

OTHER PUBLICATIONS

Singer Instruments & Control, "SM Series LVDT," Catalog of Singer Instruments & Control, LTD. Year 2003, 1 page.

Micro Strain, "Differential Variable Reluctance Transducer," Catalog of Micro Strain, pp. 1 & 2.

Analog Devices, "The LVDT Signal Conditioner," Catalog of Analog Devices for product AS598. pp. 1-16.

David S. Nyce, "The LVDT: A Simple and Accurate Position Sensor," Aug. 2005 Sensor Technology and Design. pp. 1-7.

Phillips Medical Systems, "FM-2 Antepartum Portable Fetal Monitor," Catalog of Phillips Medical Systems, pp. 1-4.

* cited by examiner

US 7,703,334 B2

BANDAGE TYPE SENSOR ARRANGEMENT AND CARRIER ASSEMBLY THEREFORE, AND METHOD OF MANUFACTURE

FIELD OF THE INVENTION

The present invention relates in general to pre-packaged sensors for monitoring movements in the form of deformations and displacements, and more particularly to sensor arrangements that can be readily attached to flexible membranes such as skin, and to carrier assemblies for the sensors.

BACKGROUND OF THE INVENTION

With the ever increasing growth of automated systems used in industrial and medical systems, there is the need for new, low cost and improved sensor apparatus or appliance and means for applying the sensors to substrates to detect movements thereof and for maintaining the sensors in place during tests. In the field of medicine there is continued research and development underway for measuring body internal and external physiological properties by non-intrusive means. This is particularly so as the sensors become miniaturized so as to be attached to the body and be worn with minimal discomfort, allowing the patient a significant amount of freedom of movement without impacting the tests underway.

As the sensors are reduced in size, it becomes more difficult to attach the sensors to the body, particularly if the sensors are in the form of at least two separate movable parts that need to be kept together in a predetermined relationship as they are secured in place for use. Furthermore, depending upon the application of the sensor function and the duration of attachment, it is desirable to have a cover for the sensor so as to reduce the likelihood sensor is moved or dislodged.

A good deal of medical tests made on the body are now performed by nurses and technicians. It is therefore important to simplify the application of the sensors. Further it is desirable if the cost of the sensor and application apparatus therefore can be manufactured to be cost effective as entirely disposable or reusable in part.

Disposable probes, or probes reusable in part, have been developed in the area of oximetry, the study and measurement of oxygen status of blood flow, that are readily attachable and detachable to patients and are disposable units or disposable in part. These probes include a light emitter and a light detector that are placed on opposite sides of a finger, toe or earlobe and the blood oxygen saturation level is detected by the differential absorption of the light waves at several wavelengths. Examples of such probes are disclosed in the U.S. Pat. No. 5,170,786, issued on Dec. 18, 1992 to Thomas et al and entitled "Reusable Probe System," and U.S. Pat. No. 7,039,449, May 2, 2006 to Ammar Al-Ali and entitled "Resposable Pulse Oximetry Sensor." However these sensors are not involved in measuring movements.

In a pending U.S. patent application Ser. No. 11/321,161, filed on Dec. 29, 2005, entitled Sensor for Monitoring Movements, Apparatus and Systems Therefore, and Method for Manufacturing and Use, for the same inventor William T. Cochran, and owned by the same entity that owns the present application, a bandage type arrangement for a sensor for detecting movement is disclosed. The bandage type arrangement includes a flexible tape with a thin resilient plastic nodule type projection that partially encases the sensor. The nodule includes two caps or projections extending there from that loosely capture the ends of the sensor keeping the sensor parts in place. When applying the bandage type senor arrangement, an adhesive is applied to the opposite free ends of the sensor and the nodule depressed to flex and urge the glued ends of the sensor ends against the substrate under test and adhere thereto, and then the nodule is released to flex back and away from the sensor allowing the sensor parts to move with changes in the substrate.

Although the nodule type bandage sensor arrangement is satisfactory, a lower cost and simplified version is also desirable.

BRIEF DESCRIPTION OF THE INVENTION

The apparatus and methods are disclosed concerning a disposable, or partially disposable, bandage type sensor arrangement or appliance and a carrier assembly therefore. A sensor having at least two movable parts is adapted to be captured by the carrier assembly and held in place until the sensor is to be attached to a substrate to monitor deformations or movements. In one example, the carrier assembly is formed from a thin flexible material and includes at least two pads adapted to adhere to the sensor parts. The carrier assembly may also be formed of a more rigid material and may include an activation method in which a portion of the carrier assembly is detachable providing free movement of the sensor parts. The pads are connected to the rest of the carrier assembly by structure having a readily detachable arrangement in the form of perforation or tear lines, and the like, to allow the pads to be readily separated from the rest of the carrier assembly when activating the sensor. In accordance of one embodiment of the invention, the sensor can be used with the carrier assembly alone. In accordance with another embodiment of the invention the sensor can be used with a bandage type cover formed with an arch over the sensor. The carrier assembly includes a number of extensions located adjacent the pads and that are also connected to the rest of the carrier assembly by a readily detachable arrangement in the form of tear or perforations, and the like, so as to be easily separated. The extensions are adhered to the cover and cooperate with the cover to keep the sensor in place when attached to the substrate to be monitored.

DETAILED DESCRIPTION OF THE INVENTION

Figure 1:
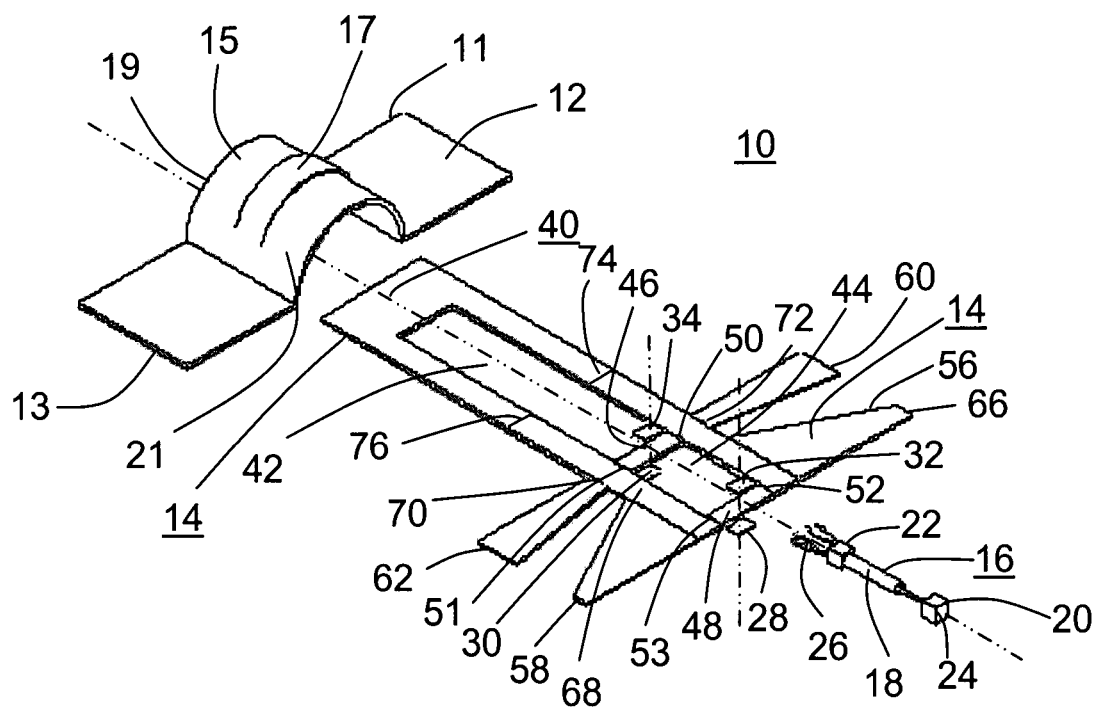
FIG. 1 is an exploded view of an embodiment of the bandage type sensor arrangement of the invention.

The bandage type sensor arrangement 10 of FIG. 1 includes a flexible bandage cover 12, a sensor carrier assembly 14 and a sensor 16 including two movable components 18 and 20 to provide indications of displacement there between. The bandage cover 12 includes an arched portion 15 having a stiffened portion 17 running along the center of the arched portion extending toward opposite ends of the bandage 11 and 13, and with flexible portions 19 and 21 on opposite sides of the stiffened portion 17. The stiffened portion 17 is formed by the application of an epoxy type cement. The bottom of the cover 12 with ends 11 and 13 include an adhesive for adhering the carrier assembly to a substrate to be tested.

The sensor 16 includes two mounts 22 and 24 attached to the components 18 and 20 respectively. Electrical connections to sensor coil portion 18 are provided by the wires 26 that may be tucked away under the bandage during installation so as to reduce stress on the sensor. Alternately the wires can terminate in a connector that can be secured to the substrate (not shown). The sensor 16 can be of the type disclosed in a pending U.S. patent application Ser. No. 11/321,161, filed on Dec. 29, 2005, entitled "Sensor for Monitoring Movements, Apparatus and Systems Therefore, and Method for Manufacturing and Use," for the same inventor William T. Cochran and assigned to the same entity as owns the present application, and is incorporated herein by reference.

The sensor mounts 22 and 24 are adapted to be secured to the carrier assembly 14 by the adhesive pads 32 and 34, respectively, and the mounts 22 and 24 are also adapted to be secured to a substrate to be monitored by the adhesive pads 28 and 30. Alternatively instead of the adhesive pads 28 and 30, the mounts 22 and 24 may receive an application of an adhesive prior to mounting.

Figure 2:
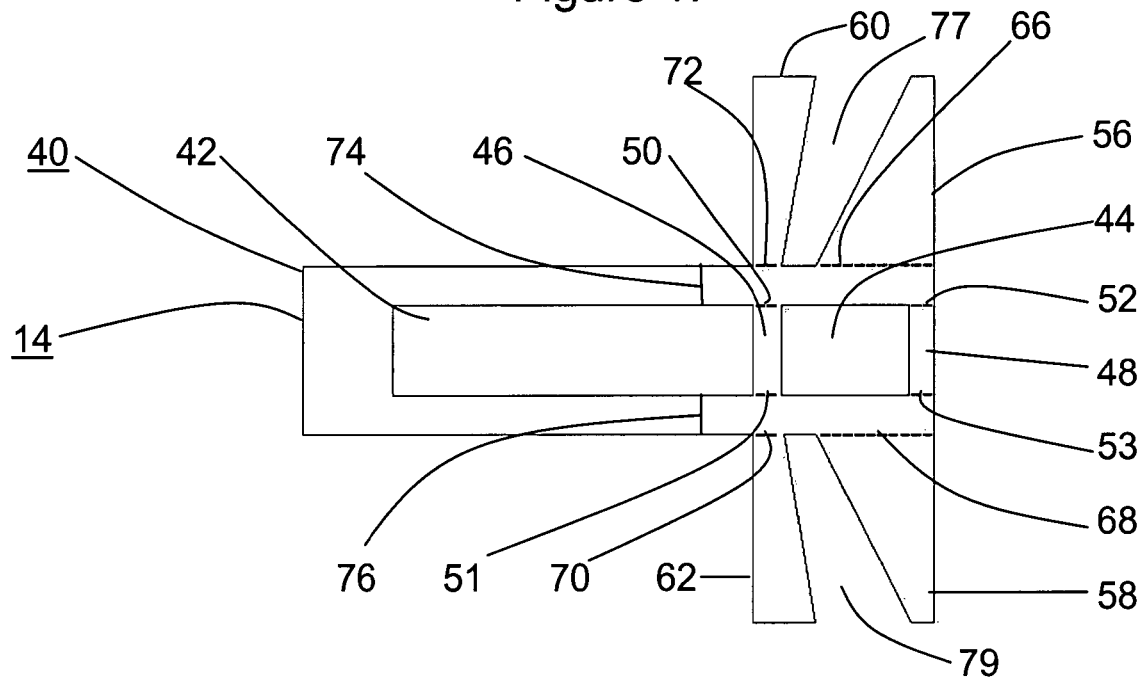
FIG. 2 is the top view of an embodiment of a carrier assembly for the sensor arrangement.
Figure 3:
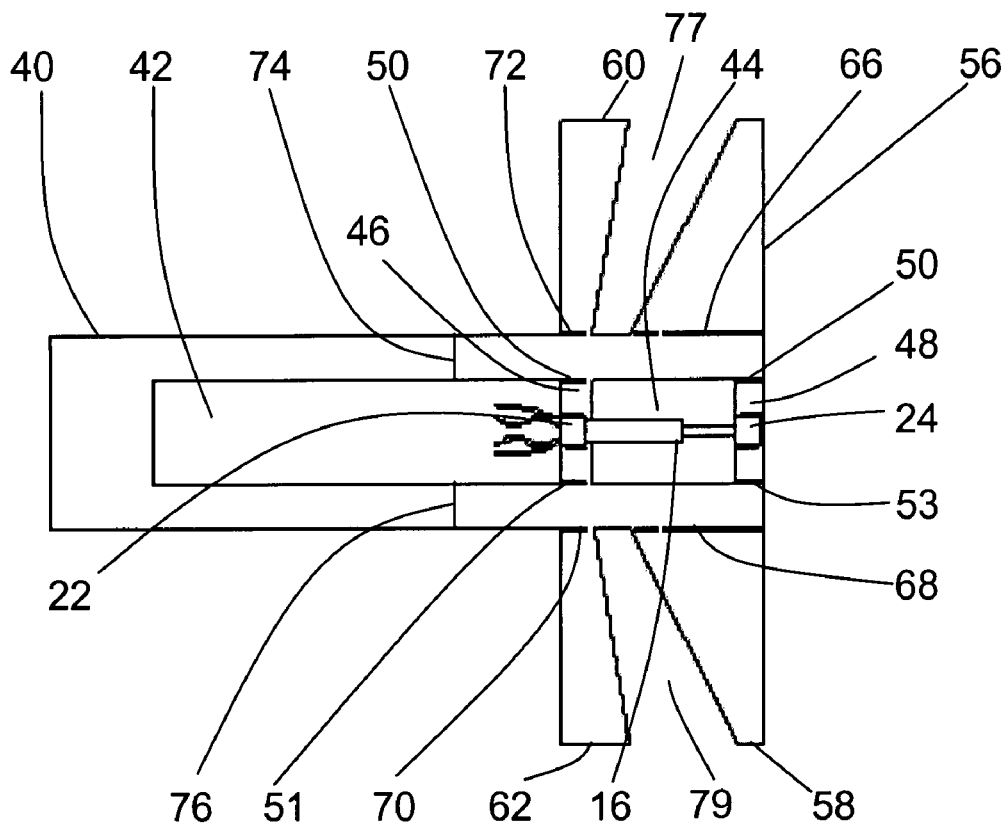
FIG. 3 is the top view of the carrier assembly of FIG. 2 with the sensor mounted thereon.

As illustrated in FIGS. 1, 2 and 3, the carrier assembly includes an elongated body 40 of a flexible material, such as paper, latex, and the like, being formed with two apertures 42 and 44. Two pads 46 and 48 are attached to the body 40 a via readily detachable structure such as the perforation or tear lines 50, 51, 52, and 53. Extending outward from the body 40 is a first set of larger extensions 56 and 58 or flanges adjacent aperture 44 and pad 48, and a second set of smaller extensions 60 and 62 or wings adjacent pad 46. The connections of the extensions 56, 58, 60 and 62 are made by a readily detachable arrangement such as the perforations, threaded break lines, or tear lines 66, 68, 70 and 72. The carrier assembly body 40 also includes a pair of fold lines 74 and 76 extending from opposite sides of the aperture 42 to the outer edge of body 40 allowing the body 40 to be folded at the fold lines. In FIG. 2, a pair of cut outs 77 and 79 are formed in the carrier assembly through which an adhesive on the cover 12 may extend to be secured to the substrate under test. The cut outs 77 and 79 may be preferentially designed for freedom of movement of the substrate under test. Alternately, the adhesive on the cover 12 may be positioned to be in contact only with extensions 56, 58, 60, and 62. In FIG. 3, the sensor 16 is illustrated with the mounts 22 and 24 attached to the detachable pads 46 and 48, respectively. The extensions 56, 58, 60, and 62 may include an adhesive on the side extending away from the cover 12 to be used to adhere to a substrate to be monitored once the bandage type sensor is applied. The sensor arrangement may include a protective detachable sheet (not shown) adhering to the extensions 56, 58, 60 and 62 and the bottom of cover 12 via cut outs 77 and 79 that can be removed prior to use.

Figure 4:
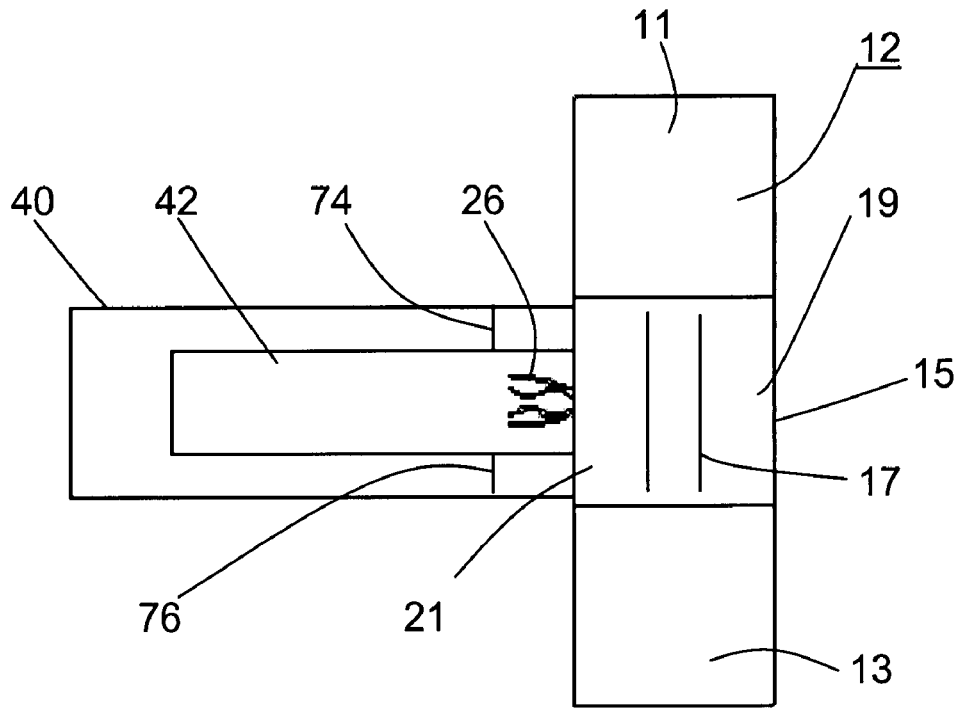
FIG. 4 is an assembled top view of the bandage type sensor arrangement of FIG. 1 with a cover in place.
Figure 5:
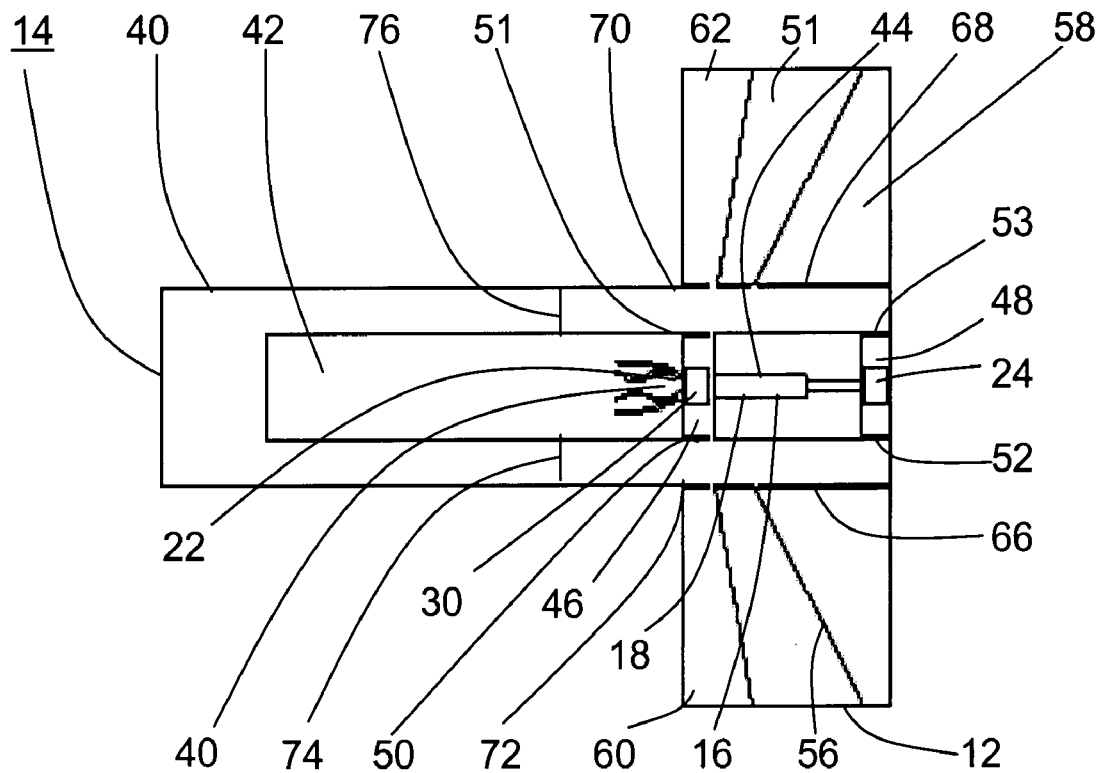
FIG. 5 is the assembled bottom view of the bandage type sensor arrangement of FIG. 1.
Figure 6:
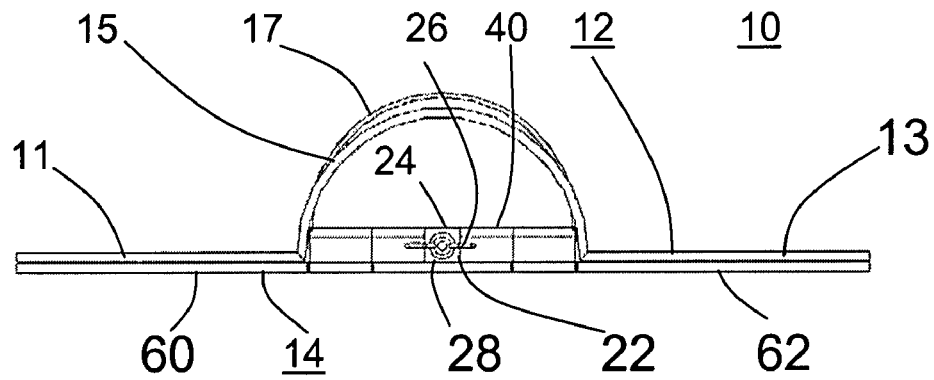
FIG. 6 is the assembled front view of the bandage type sensor arrangement of FIG. 1.
Figure 7:
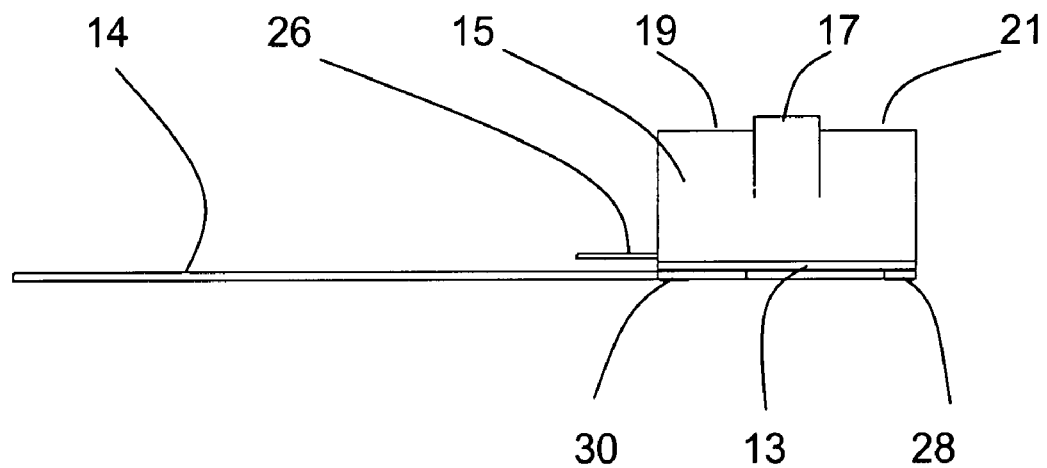
FIG. 7 is the assembled side view of the bandage type sensor arrangement of FIG. 1.

The assembled bandage type sensor 10 as shown in FIGS. 4, 5, and 7, illustrates a portion of the carrier assembly 14 extending beyond the cover 12 when first applied to a substrate prior to activation. In the side view of FIG. 6 the sensor mount 22 is attached to an adhesive pad 28. The sensor 16 as shown in FIG. 5 is connected to a substrate via the adhesive pads 28 and 30 to mounts 22 and 24 to the detachable pads 46 and 48. The sensor mounts 22 and 24 extend from the rest of the carrier assembly 14 and are adapted to make contact with the substrate to be monitored, and be attached thereto by the adhesive pads 28 and 30 or by the application of an adhesive.

Figure 8:
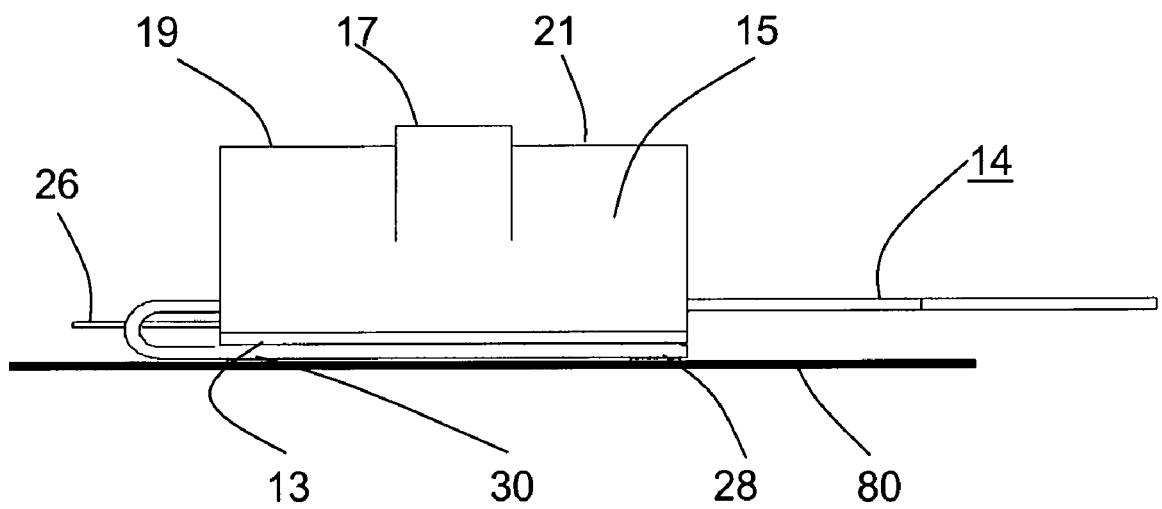
FIG. 8 is the assembled side view of the bandage type sensor arrangement of FIG. 1 with a portion of the carrier assembly folded under the bandage cover prior to activation.
Figure 9:
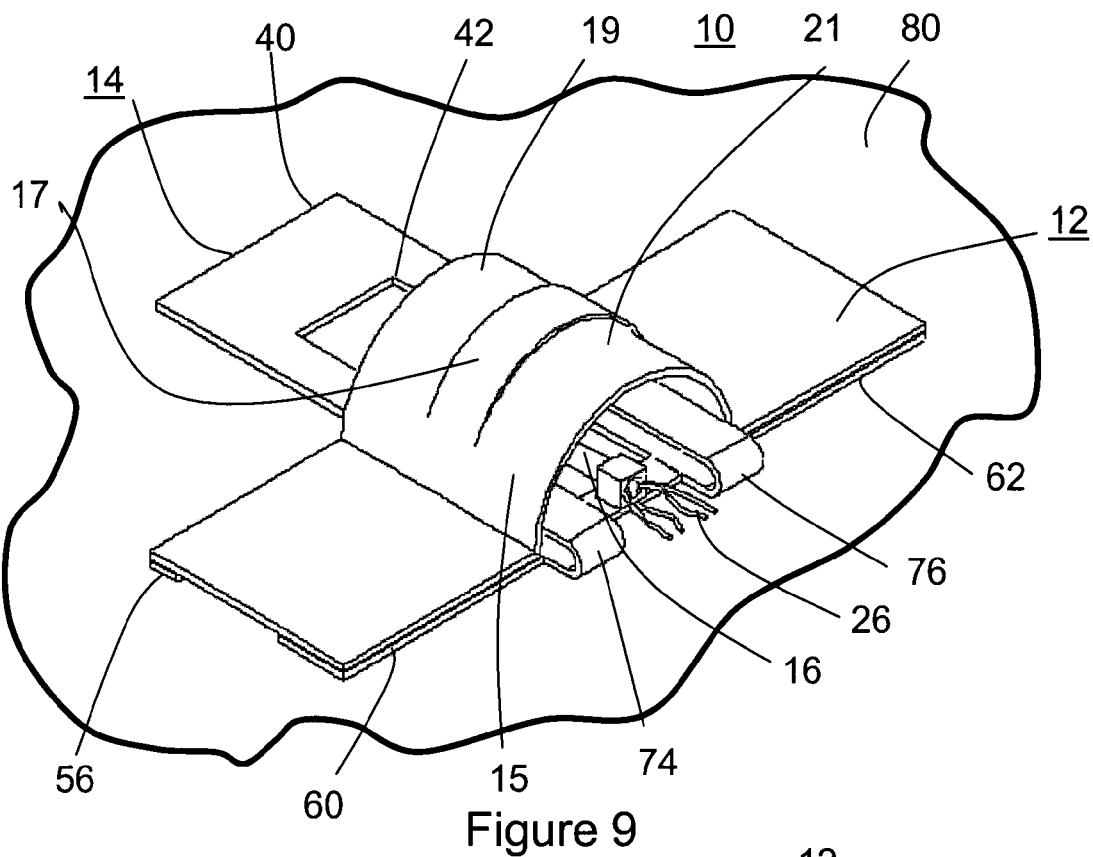
FIG. 9 is a three dimensional side view of the bandage type sensor arrangement of FIG. 8.
Figure 10:
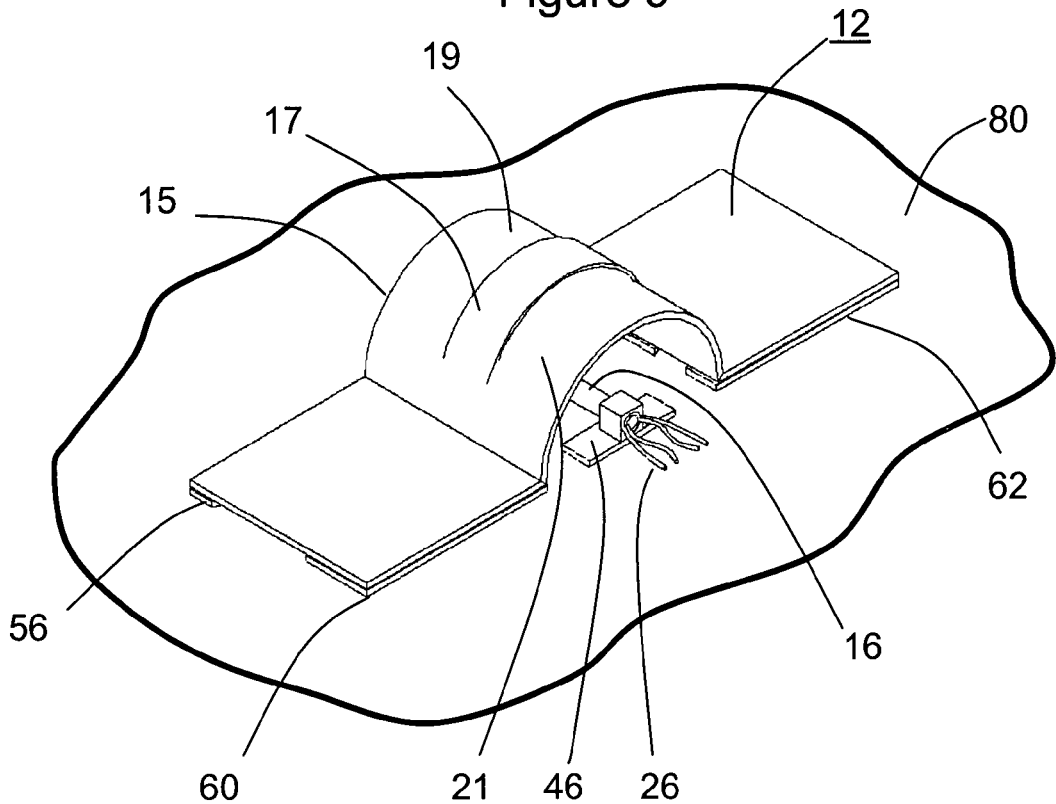
FIG. 10 is a three dimensional view of the bandage type sensor arrangement of FIG. 9 with part of the carrier assembly detached and the sensor secured to a substrate.
Figure 11:
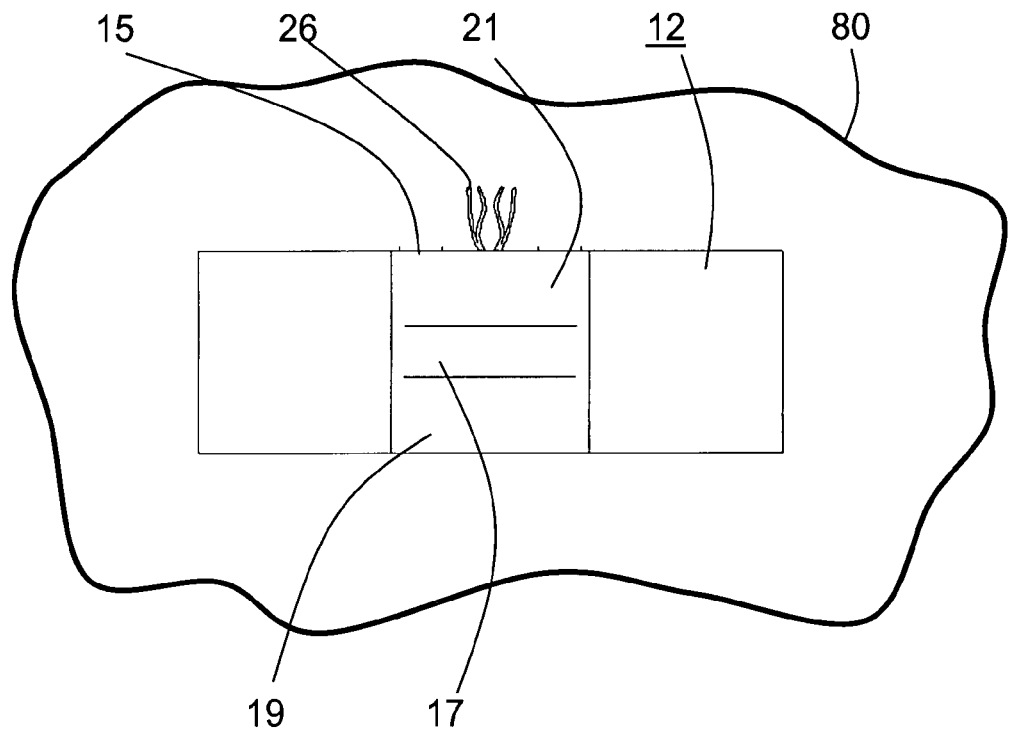
FIG. 11 is the top view of the bandage type sensor arrangement of FIG. 9 with the sensor arrangement secured to a substrate.
Figure 12:
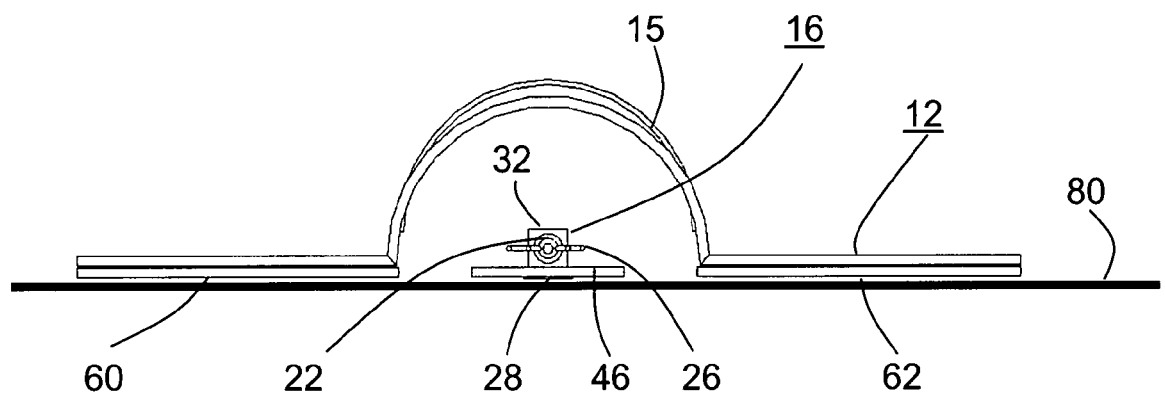
FIG. 12 is the end view of FIG. 10 after detachment from the sensor.
Figure 14:
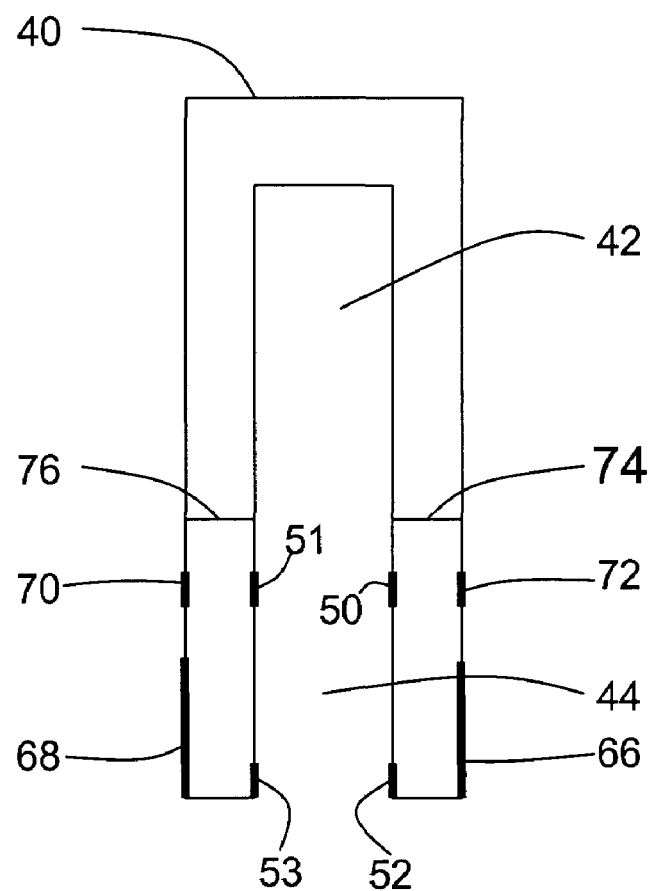
FIG. 14 is a top view of the detachable portion of the carrier assembly after being removed from the bandage type sensor arrangement.

Prior to the connection of the bandage type sensor 10 to a substrate to be monitored, the end 40 of the carrier assembly 14 is folded over along the fold lines 74 and 76 (FIG. 3) while being tucked under the cover arch 15 as shown in FIGS. 8 and 9. The sensor is mounted on a substrate by pressing the flexible portions 19 and 21 of the cover arch 15 together with the thumb and a finger and urging the sensor arrangement in place against the substrate so that the adhesive pads 28 and 30 and the extensions or flanges 56, 58, 60 and 62 engage the substrate. Thereafter a part of the carrier assembly 14 is removed by pulling it away along the perforated or tear lines 50, 51, 52, 53, 66, 68, 70 and 72 (shown in bold in FIG. 14 for the purpose of clarifying the explanation), activating the sensor and leaving behind the sensor 16 and pads 28 and 30, adhering to the substrate 80 as illustrated in FIGS. 10, 11 and 12. The portion of the cover adhesive layer over cutouts 77 and 79 not attached to the extensions may also attach to the substrate 80. Additionally, the extensions 56, 58, 60 and 62 also adhere to the substrate. The cover 12 remains in place and the arch 15 with the rigid portion 17 protects the sensor from being inadvertently moved or dislodged.

Figure 13:
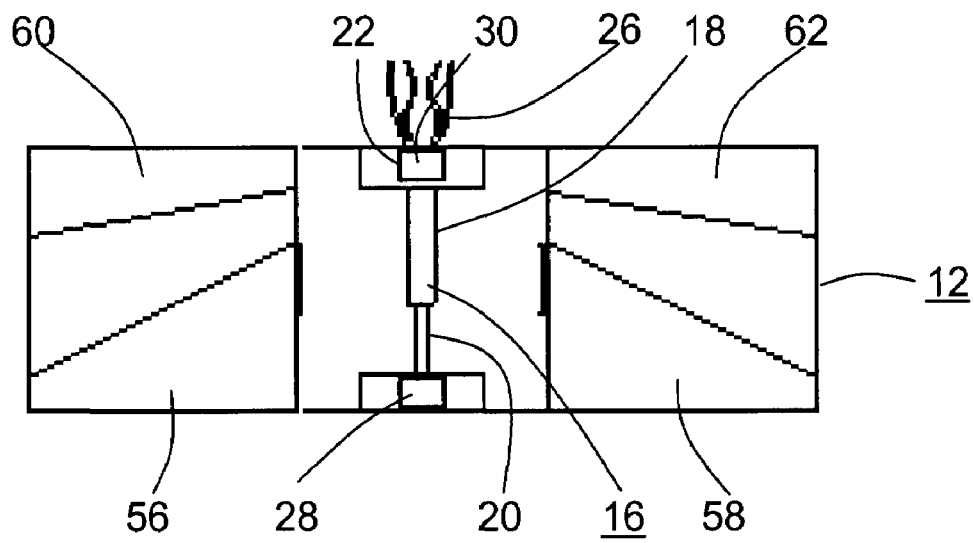
FIG. 13 is the bottom view of the bandage type sensor arrangement of FIG. 9 viewed from the substrate after activation.

It should be noted with regards to the bottom view of FIG. 13 after activation, the extensions 60 and 62 are in the general form of a triangle wherein a smaller corner extends from the carrier body 40 adjacent the mount 22. The smaller size of the corners of extensions 60 and 62 reduces the impact of the sensor has on the movement of the mount 22 and the substrate.

Figure 15:
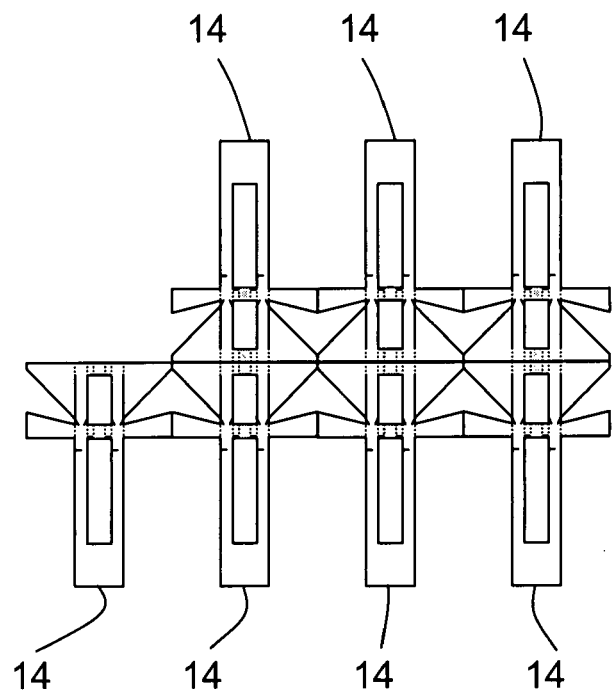
FIG. 15 is a top view of multiple carrier assemblies printed on flexible material to be cut away for use in assembling the bandage type sensors.

Multiple carrier assemblies 14 can be printed on a sheet of flexible material as shown in FIG. 15. The sheet is stamped to include the perforation or tear lines and fold lines, and cut away to form individual carrier assemblies.

Figure 16:
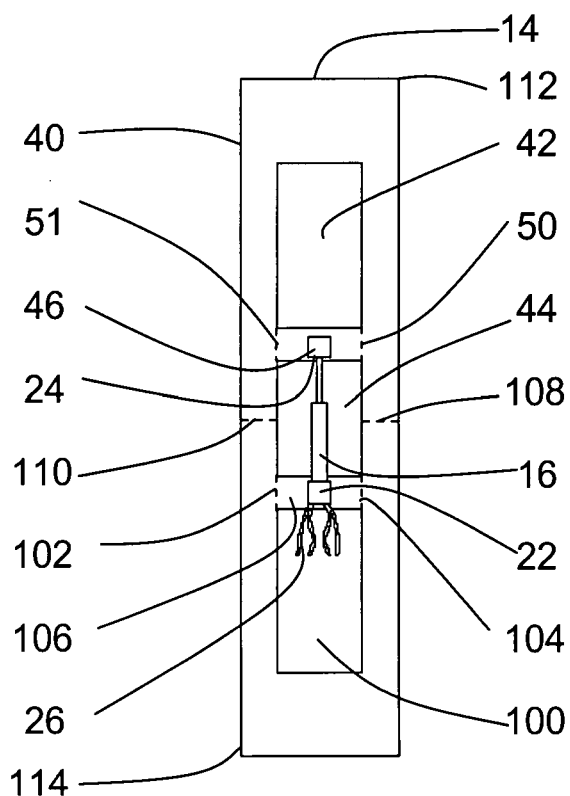
FIG. 16 is a top view of a second embodiment of the carrier assembly with the sensor attached, for use with or without a bandage cover.
Figure 17:
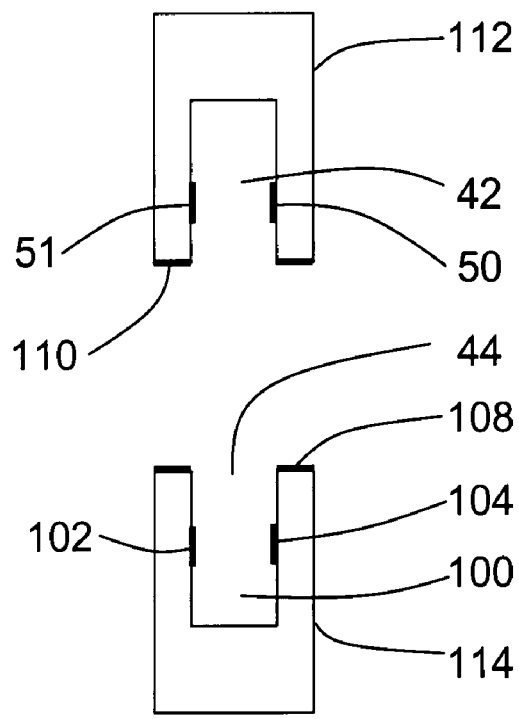
FIG. 17 is the top view of the removable part of the carrier assembly of FIG. 16 detached from the sensor after installation.
Figure 18:
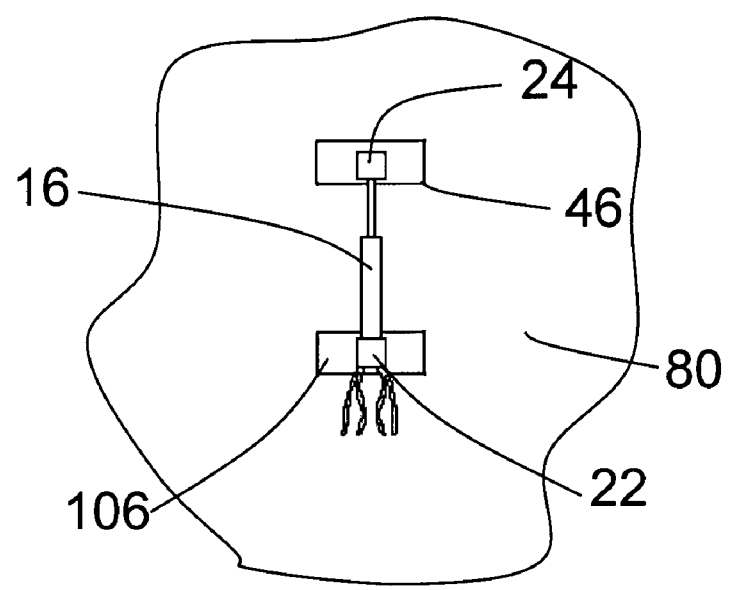
FIG. 18 illustrates the sensor attached to a substrate after the carrier assembly of FIG. 16 is removed.
Figure 19:
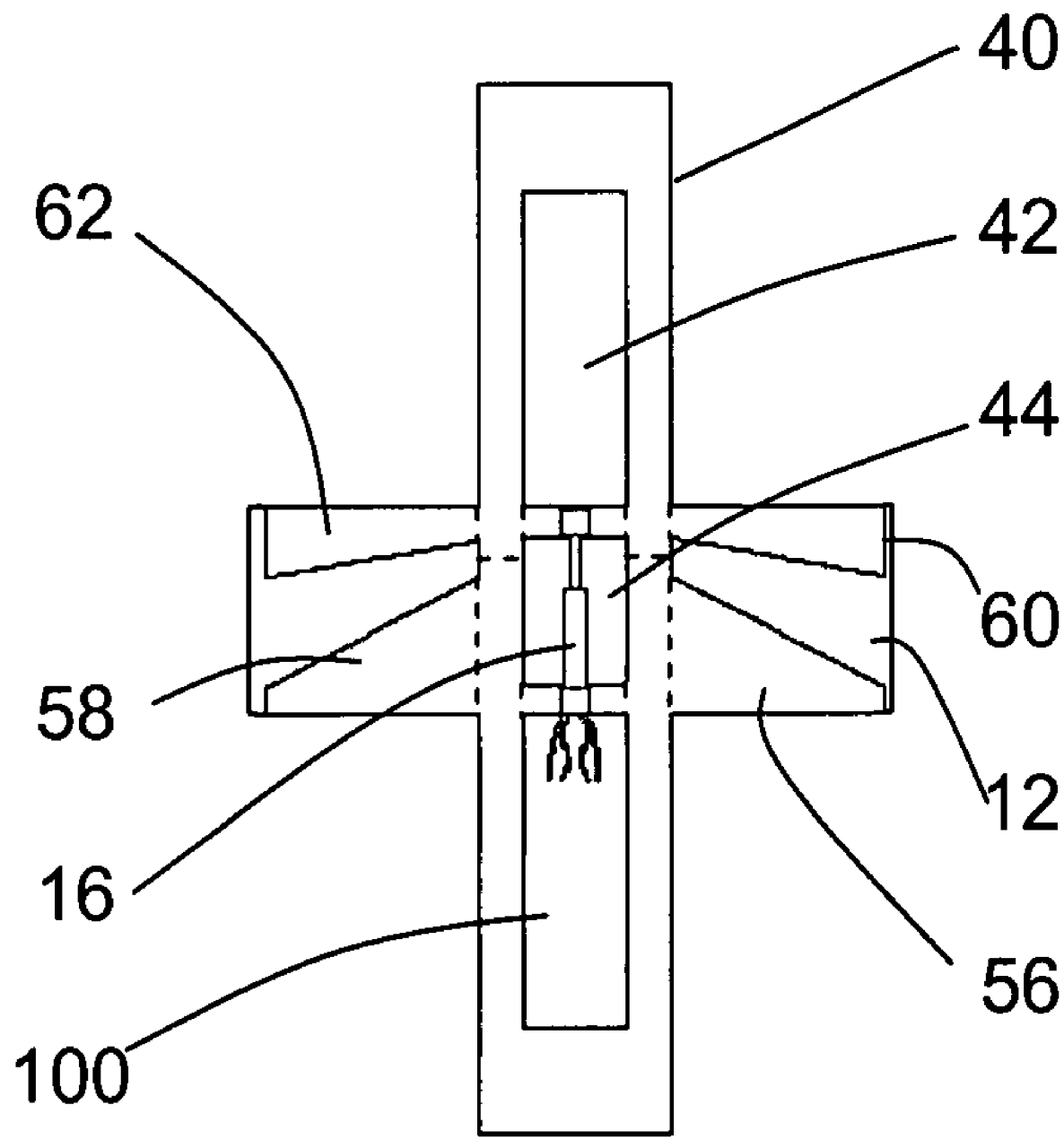
FIG. 19 is a bottom view of an embodiment of the bandage type sensor arrangement with the carrier assembly of FIG. 16 including the sensor cover.

In a further embodiment of the invention, the carrier assembly 14 of FIG. 16 is adapted for use with the bandage cover 12, or without the bandage cover as a cost reduced model. For ease of explanations, where practical, the same reference numerals will be used for similar items as in the prior Figures. The carrier assembly 14 of FIGS. 16-19 is formed with a third aperture 100 and a readily detachable pad 106 with the perforated or tear lines 102 and 104 on opposite sides of the detachable pad 106 extending between apertures 44 and 100. The carrier assembly also includes the perforation or tear lines 108 and 110 across the body 40 on opposite sides of the aperture 44. The opposite parts 112 and 114 can be detached from the rest of the assembly when mounting the sensor 16 on a substrate 80 by using fingers to urge the sensor mounts 22 and 24 against the substrate and separating the parts 112 and 114 by pulled them apart and away as illustrated in FIG. 17, leaving the sensor 16 attached to the substrate 80 as illustrated in FIG. 18 without the protective cover 12. However it should be understood that the carrier assembly of FIGS. 16 and 17 could also be used with the cover 12 as shown in the bottom view of FIG. 19.

The bandage type sensor arrangement can be easily applied to a substrate, such as skin, by a technical or nurse, without the aid of a doctor. Once the sensor 16 is in place and kept in place by fingers, the carrier assembly 14 need merely be removed and the sensor will be connected to the substrate and activated to make measurements. In the low cost embodiments of FIGS. 16-18, the sensor arrangement 10 can be used without the cover 12. Further, for added cost savings, the sensor 16 could be detached after use, sterilized and mounted to another carrier assembly 16 for subsequent use.

Specific applications and exemplary embodiments of the invention have been illustrated and discussed, which provides a basis for practicing the invention in a variety of ways and in a variety of applications. Numerous variations are possible within the scope of the invention. Features and elements associated with one or more of the described embodiments are not to be construed as required elements for all embodiments. Other changes and modifications in the specifically described embodiments can be carried out without departing from the principals of the invention that is intended to be limited only by the scope of the appended claims.

What is claimed:

1. A bandage type sensor for application to a flexible substrate for monitoring deformation of the substrate comprising:
   a sensor having at least two movable parts relative to each other to provide indications of displacements there between;
   a carrier assembly comprising a thin flexible material including at least first and second pads having a readily detachable connection to the substrate, each pad being adapted to receive an adhesive for attachment of the pads to separate sensor parts, and a cover extending over the sensor and portions of the carrier assembly, and secured to parts of the carrier assembly,
   wherein the cover includes an adhesive for attaching to portions of the carrier assembly excluding the pads, and that portions of the carrier assembly include an adhesive for connection of the bandage type sensor to the substrate to be monitored, and wherein the carrier assembly includes flanges on one end thereof and adjacent to one pad and includes tear lines for detaching the flanges from the rest of the carrier assembly.

2. A bandage type sensor for application to a flexible substrate for monitoring deformation of the substrate comprising:
   a sensor having at least two movable parts relative to each other to provide indications of displacements there between;
   a carrier assembly comprising a thin flexible material including at least first and second pads having a readily detachable connection to the substrate, each pad being adapted to receive an adhesive for attachment of the pads to separate sensor parts, and a cover extending over the sensor and portions of the carrier assembly, and secured to parts of the carrier assembly,
   wherein the cover includes an adhesive for attaching to portions of the carrier assembly excluding the pads, and that portions of the carrier assembly include an adhesive for connection of the bandage type sensor to the substrate to be monitored and wherein the carrier assembly includes flanges on one end thereof and adjacent to one pad and includes tear lines for detaching the flanges from the rest of the carrier assembly, and wherein the carrier assembly includes first and second wings extending from the carrier assembly adjacent to the other pad and including tear lines for detaching the wings from the carrier assembly and wherein the wings are significantly smaller than the flanges.

* * * * *